United States Patent
Bauer et al.

(10) Patent No.: US 6,806,379 B2
(45) Date of Patent: Oct. 19, 2004

(54) PREPARATION OF ALKYLAMINES

(75) Inventors: Andreas Bauer, Kirchdorf (DE); Herbert Jekat, Frasdorf (DE); Jochen Rauch, Kastl (DE); Peter John, Burghausen (DE); Wolfgang Kohlmann, Munich (DE); Volker Frey, Burghausen (DE); Bernd Pachaly, Mehring-Oed (DE)

(73) Assignee: Consortium fuer elektrochemische Industries GmbH, Munich (DE)

( * ) Notice: Subject to any disclaimer, the term of this patent is extended or adjusted under 35 U.S.C. 154(b) by 58 days.

(21) Appl. No.: 10/331,317

(22) Filed: Dec. 30, 2002

(65) Prior Publication Data

US 2003/0130543 A1 Jul. 10, 2003

(30) Foreign Application Priority Data

Jan. 10, 2002 (DE) ......................................... 102 00 656

(51) Int. Cl.⁷ ............................................... C07C 29/06
(52) U.S. Cl. ........................ 556/413; 564/481; 564/483
(58) Field of Search ................................ 564/481, 483; 556/413

(56) References Cited

U.S. PATENT DOCUMENTS

| | | |
|---|---|---|
| 4,234,502 A | 11/1980 | Kappler et al. |
| 4,234,503 A | 11/1980 | Kappler et al. |
| 5,808,123 A | 9/1998 | Balduf et al. |

FOREIGN PATENT DOCUMENTS

| | | |
|---|---|---|
| DE | 27 49 316 | 8/1978 |
| DE | 10 058 620 | 5/2002 |
| EP | 0 849 271 A2 | 6/1998 |

OTHER PUBLICATIONS

Derwent Abstract corresponding to DE 2 749 316 (AN 1978–63599A).

Derwent Abstract corresponding to DE 10 058 620 (AN 2002–501978).

*Primary Examiner*—Brian Davis
(74) *Attorney, Agent, or Firm*—Brooks Kushman P.C.

(57) ABSTRACT

A continuous process for preparing alkylamines comprises reacting continuous streams of ammonia and alkyl halide in a molar ratio of at least 10:1 in a pressure reactor. The ultimate reaction mixture has a temperature of >80° C., a pressure of >40 bar and an ammonium halide content of >1% by weight, and comprises two phases (A) a first phase comprising at least 75% by weight of the total amount of ammonium halide formed, and (B) a second phase comprising at least 80% by weight of the total amount of alkylamine formed.

The first and second phases are separated, and an alkylamine product is recovered therefrom.

20 Claims, No Drawings

PREPARATION OF ALKYLAMINES

BACKGROUND OF THE INVENTION

1. Field of the Invention

The invention relates to a continuous process for preparing alkylamines from alkyl halides by reaction with ammonia under pressure.

2. Background Art

Specific alkylamines, for example 3-(triethoxysilyl)-propylamine, are of great economic interest for a variety of fields. They are used, inter alia, as adhesion promoters in casting technology and the glass fiber industry, but also as crosslinkers. A further example is provided by hexamethylenediamine which is required in large volume for preparing polyamides.

The majority of patent publications are concerned with the batchwise preparation of alkylamines from alkyl halide precursors. For example, U.S. Pat. No. 4,234,502 describes the preparation of 3-(alkoxysilyl)propyl-substituted primary and secondary amines.

EP-A-849271 relates to a continuous process for preparing 3-(trialkoxysilyl)propylamines. In this process, 3-(trialkoxysilyl)propyl chloride is mixed with ammonia in the desired ratio and the mixture heated to the reaction temperature. The mixture passes through a pressure reactor, which may optionally comprise one or more temperature zones, with a residence time sufficient for complete conversion. Particular emphasis is given to a "critical" temperature of 110° C. Below this temperature, 3-(trialkoxysilyl) propylamine hydrochloride is formed, which is dissociated by ammonia on heating to above 110° C. to release free amine and ammonium chloride. The complicated workup is effected first by cooling the reaction mixture to separate a liquid silane phase. Separation of the silane phase has to be forced in some cases by adding a solvent. After separating the organic phase from the ammonium chloride-containing ammonia phase by means of extractors (mixer-settlers), the organic phase is processed distillatively. To remove the ammonium chloride, a substream of ammonia phase is depressurized, the ammonia released is condensed again, compressed, and recycled into the process, and the precipitated salt is isolated.

The known solubilities of ammonium halides in liquid ammonia may, depending on the temperature, be up to 80% by weight (iodide) at 55° C., and even at −40° C. are at least 10% by weight (chloride). Substantial separation of ammonium halides dissolved in ammonia without complete evaporation of the solvent is therefore very difficult.

SUMMARY OF THE INVENTION

It is accordingly an object of the invention to provide an improved continuous process for preparing aminoalkyl compounds which allows selective and continuous separation of the individual reaction products from the reaction mixture without adding extraneous materials. These and other objects are accomplished by the process of the subject invention.

DETAILED DESCRIPTION OF THE PREFERRED EMBODIMENT(S)

The invention provides a continuous process for preparing alkylamines in which continuous streams of ammonia and alkyl halide in a molar ratio of at least 10:1 are reacted in a pressure reactor. The ultimate reaction mixture has a temperature of >80° C., a pressure of >40 bar and an ammonium halide content of >1% by weight, and comprises two phases:

(A) a first phase which comprises at least 75% by weight of the total amount of ammonium halide formed, and
(B) a second phase which comprises at least 80% by weight of the total amount of alkylamine formed, which are then separated.

The process is based on the surprising discovery that the ultimate reaction mixture (the reaction mixture after the reaction has ended), when at a temperature of >80° C., a pressure of >40 bar and an ammonium halide content of >1% by weight, separates into a previously undescribed liquid phase (A) which comprises at least 75% by weight of the total amount of ammonium halide formed and at most 20% by weight of the total amount of alkylamine and ammonia formed. The ammonia phase (B) which forms at the same time, accordingly comprises at most 25% by weight of the total amount of ammonium halide and at least 80% by weight of the total amount of alkylamine. The ammonia phase (B) has a markedly lower density than the ammonium halide phase (A).

The process allows selective and continuous separation of the individual reaction products from the end reaction mixture without adding extraneous materials and at the same time ensures that only a small portion of the process ammonia has to be completely evaporated and recondensed. The process allows high product yields and purities to be ensured at low preparation costs.

The (A) and (B) phases may be separated from each other using common liquid-liquid separation methods by utilizing the difference in density between the phases. The pressure in the separation is preferably at least 80 and at most 400 bar. Particular preference is given to separation taking place above the critical point of ammonia (132.4° C., 112.8 bar), since under these conditions, the ammonium halide phase (A) comprises at least 85% of the total amount of ammonium halide formed and at most 10% by weight of the total amount of alkylamine formed. The ammonium halide phase (A) may optionally be extracted with pure ammonia during the separation in order to remove any residual amount of alkylamine.

Preference is given to continuously discharging phase (A), which still comprises up to 20% by weight of the total amount of alkylamine, from the process with depressurization, and preferably evaporating and recycling the ammonia present in this phase. The ammonium halide occurring in crystalline form may optionally be freed of any remaining alkylamine by washing with an organic solvent.

The ammonia phase (B), freed from the ammonium halide phase (A) and laden with the majority of alkylamine and small amounts of ammonium halide, is preferably depressurized at a lower pressure of at least 15 bar at a temperature of at least 50° C., to separate a further fluid phase (C). The liquid phase (C) comprises a large proportion of alkylamine, and small amounts of ammonium halide and ammonia, and, owing to a marked density difference, may be separated by common methods from a less dense ammonia phase (D). Preference is given to compressing the separated, pure ammonia phase (D) and recycling it into the process. After discharging the alkylamine phase (C) with depressurization, it is preferably separated continuously by rectification into its components.

The molar ratio of ammonia to alkyl halide in the reaction is preferably at least 20:1. The molar ratio of ammonia to alkyl halide is preferably at most 150:1.

Preference is given to preheating the streams of ammonia and alkyl halide before entry into the pressure reactor. The reaction temperature is preferably at least 100° C., more preferably at least 120° C., and preferably at most 400° C., more preferably at most 300° C.

Particular preference is given to carrying out the reaction in supercritical ammonia, i.e. above the critical point (132.4° C., 112.8 bar). In addition to the higher temperatures at these conditions, the low viscosity coefficients and high diffusion coefficients of the supercritical medium compared to liquid ammonia also have a positive effect on the reaction rate and selectivity.

In the process, preference is given to preparing aminoalkylsilanes from the corresponding alkyl chlorides. Preferred aminoalkylsilanes are of the general formula 1

$$(RO)_{3-n}R^1{}_nSiR^2NH_2 \tag{1},$$

where

R is an optionally fluorine-substituted alkyl or alkoxyalkyl radical having from 1 to 6 carbon atoms, $R^1$ is an optionally fluorine-substituted hydrocarbon radical having from 1 to 12 carbon atoms, $R^2$ is an optionally fluorine-substituted alkylene radical having from 1 to 20 carbon atoms in which nonadjacent methylene units may be replaced by —O— groups and n has the value 0, 1, 2 or 3.

R is preferably methyl, ethyl or propyl.

The $R^1$ radicals are preferably unsubstituted. $R^1$ is preferably a hydrocarbon radical having from 1 to 6 carbon atoms, in particular methyl, ethyl, propyl, vinyl or phenyl. The $R^2$ radicals are also preferably unsubstituted. $R^2$ is preferably an alkylene radical having from 1 to 6 carbon atoms, in particular methylene, ethylene or propylene.

All the symbols in the above formulae are each defined independently. In all formulae, the silicon atom is tetravalent. Terms such as "optionally substituted" mean substituted or unsubstituted.

EXAMPLE 1

In a pressure reactor of 35l capacity, made of corrosion-resistant material (Hastelloy B3; Hastelloy steels of the B and C series are generally suitable), streams of ammonia (14.7 kg/h) and 3-(triethoxysilyl)propyl chloride (4.0 kg/h), each preheated to 175° C., are reacted with each other at a pressure of 200 bar. After leaving the pressure reactor, the reaction mixture is heated to 190° C. and transferred to a second pressure reactor of identical design in which the conversion is completed. The average residence time in the reaction section is 60 min.

In a downstream first separation stage, a heavy, lower phase (A) is removed from the biphasic reaction mixture and transferred with depressurization to a drying apparatus. When the predominantly ammonium chloride- and ammonia-containing phase (A) is depressurized, it separates into 0.9 kg/h of solid salt, and gaseous ammonia which is recycled. The purity of the ammonium chloride obtained is 97% by weight.

The silane-containing ammonia stream (B) leaving the first separation stage is supplemented with 0.6 kg/h of fresh ammonia in order to replace the ammonia consumed in the reaction. Before entry into the second separation stage, the ammonia stream is depressurized to 125 bar and heated to 170° C. to again form a biphasic mixture. The lower silane- and ammonia-containing phase (C) is separated from the ammonia stream (D) under depressurization, and the ammonia is released in gaseous form and recycled. The crude silane is transferred to a rectification apparatus and separated therein into its components. The distillate stream of 3.0 kg/h (82% of theory) comprises 3-(triethoxysilyl)propylamine having a purity of 99% by weight. In addition, a further 0.7 kg/h of high-boiling reaction product is obtained in the bottoms of the apparatus. The ammonia stream (D) released from the second separation stage is compressed and recycled into the process.

Space-time yield (yield of product in g per hour and liter of reaction volume): 43 g/lh

EXAMPLE 2 (COMPARATIVE EXAMPLE)

In a 17 l steel-enamel autoclave equipped with a stirrer, 5800 g of liquid ammonia are charged and heated. After 1 hour, the reaction temperature of 75° C. is obtained at a pressure of 36 bar. With stirring (200 rpm), 1580 g of 3-(triethoxysilyl)propylamine are metered in during 2 hours and then stirred at 75° C. for a further 8 hours. After cooling to 50° C., the reaction mixture is depressurized and the ammonia evaporated over a period of 3 hours. The remaining crude product is separated by filtration from the ammonium chloride formed (378 g, purity 93% by weight) and then worked up by distillation under reduced pressure. The distillate obtained is 1075 g of 3(triethoxysilyl)propylamine (74% of theory, purity 99% by weight) and the distillation residue obtained is 334 g of high-boiling by-products. Space-time yield: <4.5 g/lh While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A continuous process for preparing alkylamines, comprising:
    reacting ammonia and alkyl halide in a molar ratio of at least 10:1 under pressure in a reactor, the ultimate reaction mixture prior to separation having a temperature of >80° C., a pressure of >40 bar and an ammonium halide content of >1% by weight, and comprising two phases:
    (A) a first phase comprising at least 75% by weight of the total amount of ammonium halide formed, and
    (B) a second phase comprising at least 80% by weight of the total amount of alkylamine formed,
    and separating said first and second phases at a temperature greater than 80°C.

2. The process of claim 1, wherein the separation of the first and second phases of the ultimate reaction mixture takes place above the critical point of ammonia.

3. The process of claim 1, further comprising depressurizing phase (B) to a lower pressure which is at least 15 bar at a temperature of at least 50° C., and separating:
    (C) a third phase comprising predominately alkylamine and a small proportion of ammonium halide, from
    (D) a fourth phase which comprises predominately ammonia.

4. The process of claim 2, further comprising depressurizing phase (B) to a lower pressure which is at least 15 bar at a temperature of at least 50° C., and separating:
    (C) a third phase comprising predominately alkylamine and a small proportion of ammonium halide, from
    (D) a fourth phase which comprises predominately ammonia.

5. The process of claim 1, which the molar ratio of ammonia to alkyl halide is at least 20:1.

6. The process of claim 2, which the molar ratio of ammonia to alkyl halide is at least 20:1.

7. The process of claim 3, which the molar ratio of ammonia to alkyl halide is at least 20:1.

8. The process of claim 4, which the molar ratio of ammonia to alkyl halide is at least 20:1.

9. The process of claim 1, wherein the ammonia and the alkyl halide are each preheated before entry into the reactor.

10. The process of claim 1, wherein said reacting takes place above the critical point of ammonia.

11. The process of claim 2, wherein said reacting takes place above the critical point of ammonia.

12. The process of claim 3, wherein said reacting takes place above the critical point of ammonia.

13. The process of claim 4, wherein said reacting takes place above the critical point of ammonia.

14. The process of claim 5, wherein said reacting takes place above the critical point of ammonia.

15. The process of claim 6, wherein said reacting takes place above the critical point of ammonia.

16. The process of claim 7, wherein said reacting takes place above the critical point of ammonia.

17. The process of claim 8, wherein said reacting takes place above the critical point of ammonia.

18. The process of claim 9, wherein said reacting takes place above the critical point of ammonia.

19. The process of claim 1 wherein said alkylamine is an aminoalkylsilane having the formula $$(RO)_{3-n}R^1{}_n SiR^2 NH_2$$

wherein

R is an optionally fluorine-substituted $C_{1-6}$ alkyl or $C_{1-6}$ alkoxyalkyl radical, $R^1$ is an optionally fluorine-substituted $C_{1-12}$ hydrocarbon radical, $R^2$ is an optionally fluorine-substituted $C_{1-20}$ alkylene radical in which non-adjacent methylene units may be replaced by —O—, and n is 0, 1, 2, or 3.

20. The process of claim 1 wherein said alkylamine is an alkylene diamine.

* * * * *